(12) United States Patent
Tsai et al.

(10) Patent No.: US 9,562,540 B2
(45) Date of Patent: Feb. 7, 2017

(54) CENTRIFUGAL ROTOR

(75) Inventors: Chung-Hsien Tsai, Hsinchu County (TW); Hsiao-Chung Tsai, Taoyuan County (TW); Chih-Yu Chao, Hsinchu County (TW); Ying-Lan Tsai, New Taipei (TW)

(73) Assignee: PROTECTLIFE INTERNATIONAL BIOMEDICAL INC., Taoyuan County (TW)

( * ) Notice: Subject to any disclaimer, the term of this patent is extended or adjusted under 35 U.S.C. 154(b) by 469 days.

(21) Appl. No.: 14/348,057

(22) PCT Filed: Sep. 29, 2011

(86) PCT No.: PCT/CN2011/001650
§ 371 (c)(1),
(2), (4) Date: Mar. 28, 2014

(87) PCT Pub. No.: WO2013/044412
PCT Pub. Date: Apr. 4, 2013

(65) Prior Publication Data
US 2014/0255193 A1    Sep. 11, 2014

(51) Int. Cl.
*F04D 29/22* (2006.01)
*B01L 3/00* (2006.01)
*G01N 35/00* (2006.01)

(52) U.S. Cl.
CPC ......... *F04D 29/22* (2013.01); *B01L 3/502738* (2013.01); *B01L 2200/16* (2013.01); *B01L 2300/0672* (2013.01); *B01L 2300/0803* (2013.01); *B01L 2300/0867* (2013.01); *B01L 2400/0409* (2013.01); *B01L 2400/0683* (2013.01); *G01N 2035/00158* (2013.01)

(58) Field of Classification Search
CPC  F04D 29/22; B01L 3/502738; B01L 2200/16; B01L 2300/0672
USPC ................................... 416/204 R
See application file for complete search history.

(56) References Cited

U.S. PATENT DOCUMENTS

| 5,693,233 A * | 12/1997 | Schembri | G01N 21/07 210/377 |
| 7,901,843 B2 * | 3/2011 | Sugiyama et al. | B82Y 10/00 430/5 |
| 8,562,911 B2 * | 10/2013 | Tsai | B01L 3/502753 422/400 |

FOREIGN PATENT DOCUMENTS

DE          10344229 A1    5/2005

* cited by examiner

*Primary Examiner* — Kevin Lee
(74) *Attorney, Agent, or Firm* — CKC & Partners Co., Ltd.

(57) ABSTRACT

A centrifugal rotor includes a rotor body, a diluent container, a piercing structure and a capping film. The rotor body has a receiving cavity. The diluent container is located within the receiving cavity and has a seal film. The piercing structure is located within the receiving cavity and in contact with the seal film. The capping film is located over the diluent container and the piercing structure for securing the diluent container and the piercing structure within the receiving cavity.

14 Claims, 13 Drawing Sheets

CENTRIFUGAL ROTOR

CROSS-REFERENCE TO RELATED APPLICATIONS

This application is a continuation of International application No. PCT/CN2011/001650, filed on Sep. 29, 2011, the contents of which is incorporated herein by reference.

BACKGROUND

Field of Invention

The present invention relates to a centrifugal rotor. More particularly, the present invention relates to a centrifugal rotor in biochemical analyses.

Description of Related Art

Biological analysis of blood and other specimen usually require quickly distributing liquid to perform different tests. Biochemical analysis also requires cell bodies and body fluids to be separated prior to testing to prevent from being influenced by each other. The distributing step and separation step are usually achieved by a centrifugation step, and then be manually or automatically assigned to the quantity of each sample specimen vessel. The above quantitative allocation process is not only laborious but also time-consuming. Thus, a variety of automated specimen quantitative distribution systems have been proposed to improve these labor-consuming processes.

At present, the main distribution system improvement is the use of automated quantitative centrifugal rotor. After these centrifugal rotors are used with centrifuges, quantitative distribution of the specimen, sample mixing and diluting can be performed for optical analysis purposes. Although there are already several centrifugal rotor designs, more effort is still needed to enhance the convenience and precision of performing the biochemical analysis.

Therefore, inconvenience and defects still exist in the structure and use of a conventional centrifugal rotor, and need to be further improved. In order to solve the above problems, all the venders think hard to seek a solution, but it seems that no product can effectively solve the above problems. Accordingly, how to create a new type of centrifugal rotor is one of the currently important research topics, but also become the industry improvement goals in urgent needs.

SUMMARY

It is therefore an objective of the present invention to provide an improved centrifugal rotor.

In accordance with the foregoing and other objectives of the present invention, a centrifugal rotor includes a rotor body, a diluent container, a piercing structure and a capping film. The rotor body has a receiving cavity. The diluent container is located within the receiving cavity and has a seal film. The piercing structure is located within the receiving cavity and in contact with the seal film. The capping film is located over the diluent container and the piercing structure for securing the diluent container and the piercing structure within the receiving cavity.

In order deal with the objectives of the present invention and its technical problems, the following technical features can be further implemented.

According to another embodiment disclosed herein, the piercing structure is a cover which includes a plurality of cones facing the seal film.

According to another embodiment disclosed herein, one of the cones is located at a center of the cover.

According to another embodiment disclosed herein, the cone at the center of the cover is higher than the remaining cones of the cover.

According to another embodiment disclosed herein, each cone includes at least one concave groove.

According to another embodiment disclosed herein, the cover has a concave liquid guiding area within which the cones are located.

According to another embodiment disclosed herein, the piercing structure is a piercing loop which includes a C-shaped ring and a piercing member, having an end coupled to the C-shaped ring.

According to another embodiment disclosed herein, a free end of the piercing member includes a triangular tip.

According to another embodiment disclosed herein, the piercing member protrudes out of a level within which the C-shaped ring is located except two opposite ends of the piercing member.

According to another embodiment disclosed herein, the seal film is a plastic film or a metallic film.

According to another embodiment disclosed herein, the piercing structure is located above the diluent container.

According to another embodiment disclosed herein, the receiving cavity has a bottom hole that is aligned with the diluent container.

According to another embodiment disclosed herein, the diluent container is located above piercing structure.

According to another embodiment disclosed herein, the receiving cavity has a bottom hole that is aligned with the diluent container.

The present invention has the following advantages and benefits compared with the prior art. The centrifugal rotor disclosed herein is equipped with a piercing structure to penetrate a seal film of the diluent container, rather than removing the seal film of the diluent container manually. Therefore, the piercing structure design not only makes it easier to perform biochemical analysis, and the diluted solution can be released when needed, and prevented from being volatile or contaminated.

Thus, it is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows.

DETAILED DESCRIPTION

Figure 1:
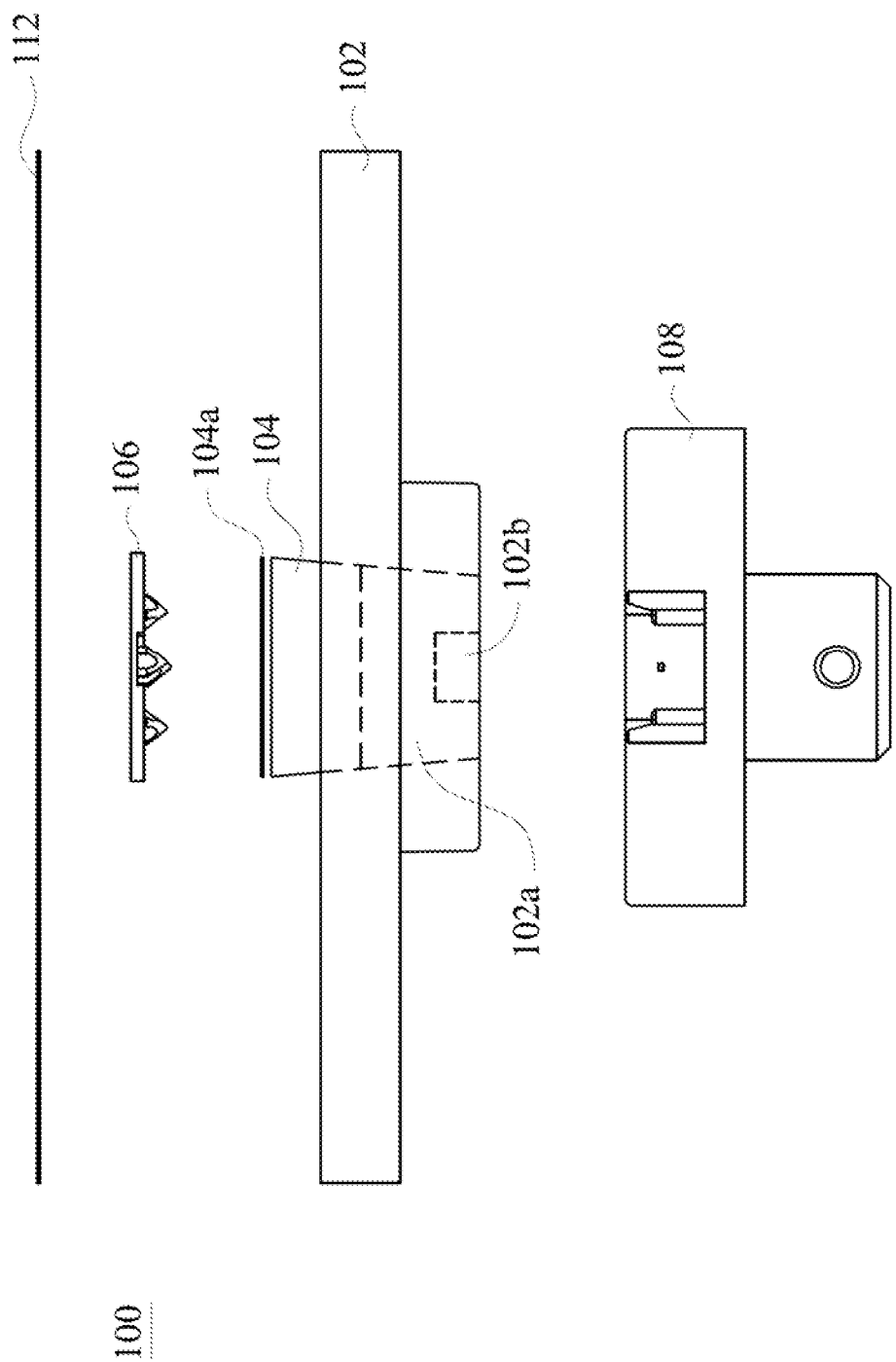
FIG. 1 illustrates an exploded view of a centrifugal rotor according to one embodiment of this invention.

Reference will now be made in detail to the present embodiments of the invention, examples of which are illustrated in the accompanying drawings. Wherever possible, the same reference numbers are used in the drawings and the description to refer to the same or like parts.

FIG. 1 illustrates an exploded view of a centrifugal rotor according to one embodiment of this invention. A centrifugal rotor 100 should be used in a centrifugal device and biochemical analysis device (not shown in the drawings) for filling and distributing biochemical sample. The centrifugal rotor 100 basically includes a rotor body 102, a diluent container 104 (contains diluents inside), a piercing structure 106 and a capping film 112. An upper part of the driving rotor 108 is used to connect with the rotor body 102, and a lower part of the driving rotor 108 is coupled with a centrifugal device such that the centrifugal device can drive the centrifugal rotor 100 to rotate so as to distribute biochemical sample, mix biochemical samples and diluents or separate cell bodies and body fluids. The rotor body 102 has a receiving cavity 102a to accommodate the diluent container 104. The diluent container 104 has a seal film 104a, e.g., an aluminum film, to seal an opening of the container so as to prevent the diluents inside from being contaminated or volatile. The receiving cavity 102a has a bottom hole 102b through which the driving rotor 108 is inserted. The piercing structure 106 is in contact with the seal film 104a and used to penetrate the seal film 104a to release the diluents inside the diluent container 104 according actual demands. The capping film 112 is covered over the diluent container 104 and the piercing structure 106 so as to secure the diluent container 104 and piercing structure 106 within the receiving cavity 102a.

Figure 2:
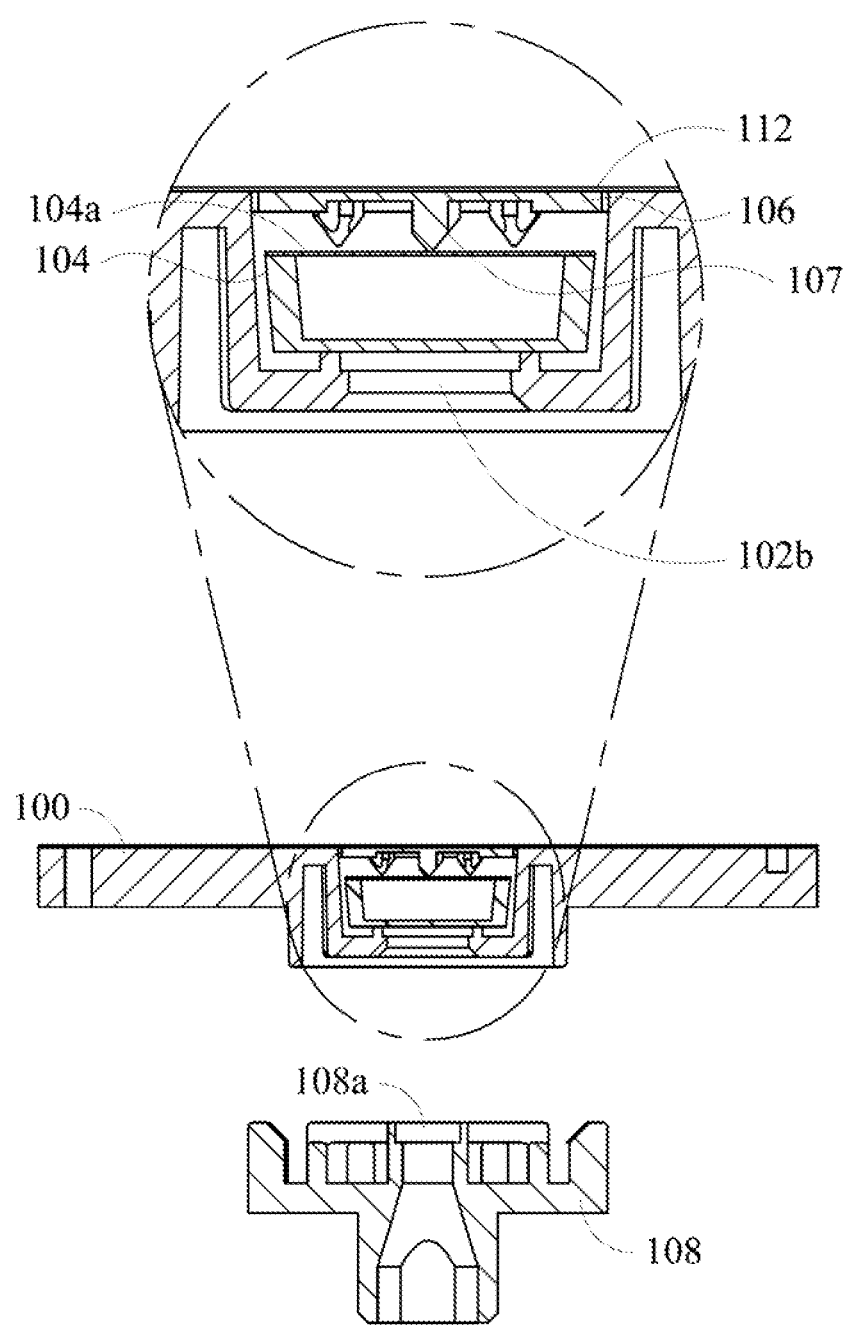
FIG. 2 illustrates a cross-sectional view of a centrifugal rotor and a driving rotor that are separated from each other according to one embodiment of this invention.
Figure 3:
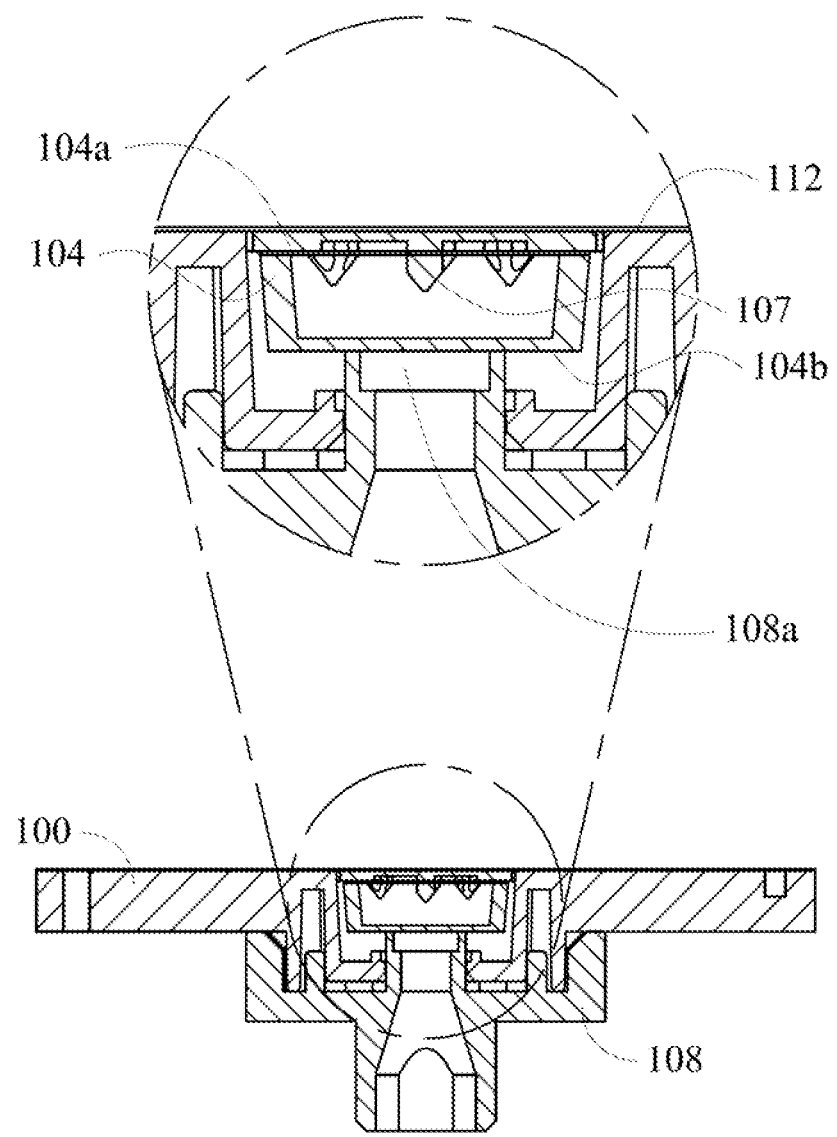
FIG. 3 illustrates a cross-sectional view of the centrifugal rotor and the driving rotor in FIG. 2 that are assembled.

Referring to both FIG. 2 and FIG. 3, FIG. 2 illustrates a cross-sectional view of a centrifugal rotor and a driving rotor that are separated from each other according to one embodiment of this invention, and FIG. 3 illustrates a cross-sectional view of the centrifugal rotor and the driving rotor in FIG. 2 that are assembled. When the centrifugal rotor 100 is not used to perform biochemical analysis, the centrifugal, rotor 100 and the driving rotor 108 are separated, and a cone 107 of the piercing structure 106 cannot penetrate the seal film 104a of the diluent container 104 without an external push (referring to FIG. 2). When the centrifugal rotor 100 is used to perform biochemical analysis, the centrifugal rotor 100 and the driving rotor 108 are assembled. A central axis 108a of the driving rotor 108 is inserted through the bottom hole 102b of the centrifugal rotor 100 and coupled with a bottom part 104b of the diluent container 104 so as to lift the diluent container 104 to enable the cone 107 of the piercing structure 106 to penetrate the seal film 104a of the diluent container 104 (referring to FIG. 3). The capping film 112 is covered over the piercing structure 106 to restrict an upward moving of the piercing structure 106 such that the cone 107 of the piercing structure 106 is able to penetrate the seal film 104a of the diluent container 104 when the diluent container 104 is lifted upwards.

Figure 4A:
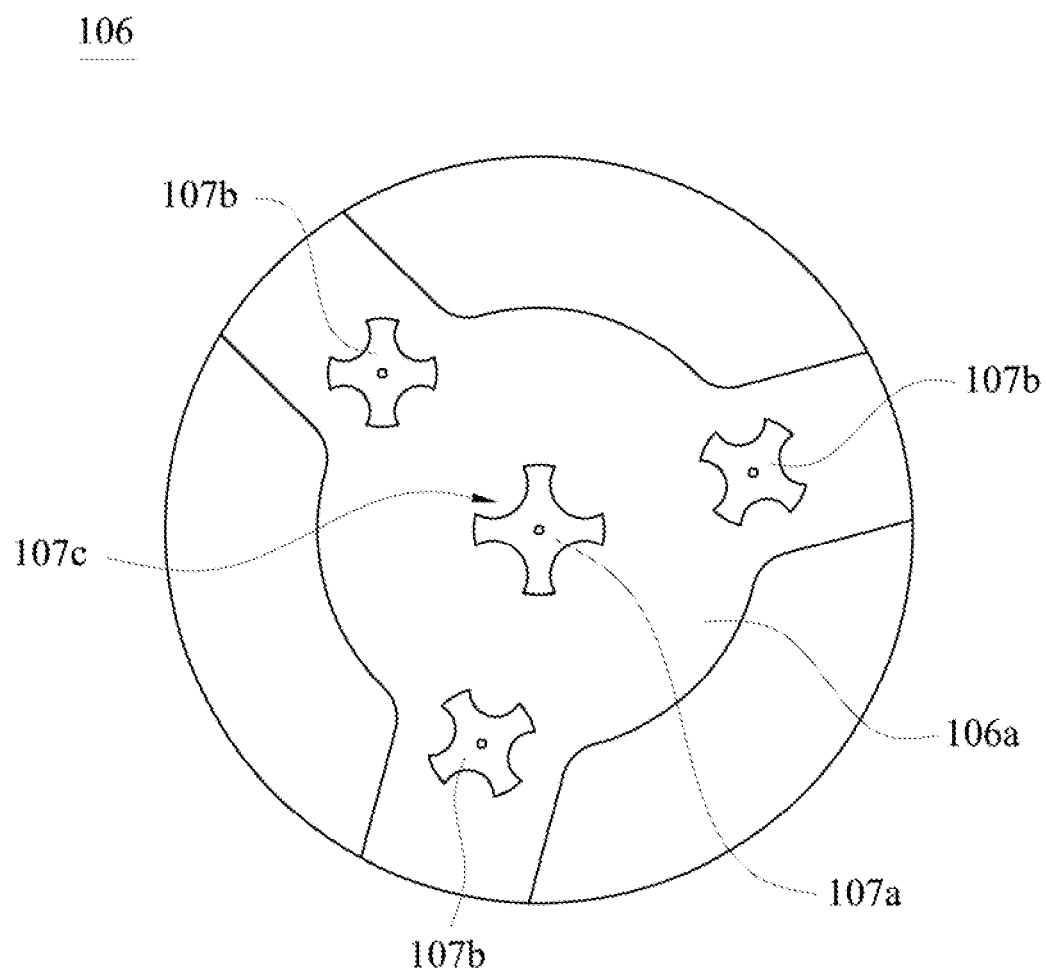
FIG. 4A illustrates a bottom view of a piercing structure according to one embodiment of this invention.
Figure 4B:
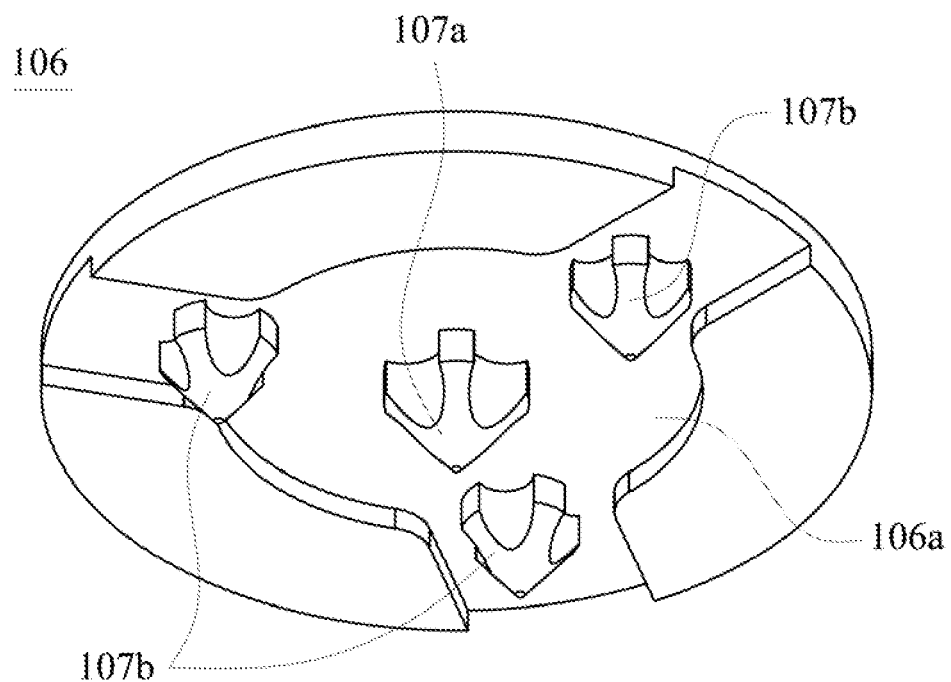
FIG. 4B illustrates a perspective view of the piercing structure in FIG. 4A.
Figure 4C:
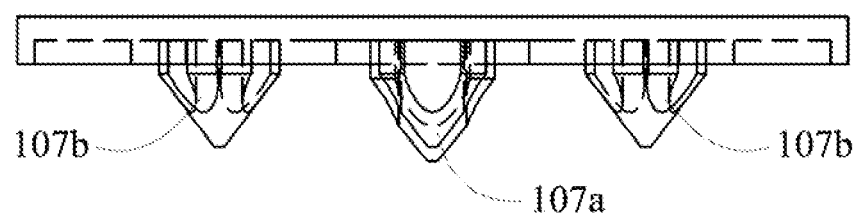
FIG. 4C illustrates a lateral view of the piercing structure in FIG. 4A.

Referring to FIG. 4A, 4B and 4C, FIG. 4A illustrates a bottom view of a piercing structure 106, FIG. 4B illustrates a perspective view of the piercing structure 106 in FIG. 4A, and FIG. 4C illustrates a lateral view of the piercing structure 106 in FIG. 4A. The piercing structure 106 is a cover which has a plurality of cones facing the seal film 104a (also referring to FIG. 2). In this embodiment, the piercing structure 106 has four cones, wherein the cone 107a is located at a center of the cover, the remaining cones 107b are located around the cone 107a, and, the cone 107a at the center of the cover is higher than the remaining cones 107b of the cover. The seal film 104a of the diluent container 104 tends to be concave and its center is usually concave to the maximum extent such that the higher cone 107a is beneficial to penetrate the seal film. However, quantities and heights of the cone are not limited to the aforesaid embodiments, e.g., more than four cones of equal heights. In this embodiment, each cone has four concave grooves 107c at its lateral surfaces. The concave groove 107c guides the diluent to flow out of an opening (i.e., penetrated by the cones) on the seal film. Each cone may include at least one concave groove to guide the diluent to flow out of the opening (i.e., penetrated by the cones) on the seal film. In addition, the cover may have a concave liquid guiding area 106a, and the cones (107a, 107b) are located within the concave liquid guiding area 106a. The concave liquid guiding area 106a aims to guide the flowed-out diluents to be easily carried out of the cover by a centrifugal force.

Figure 5:
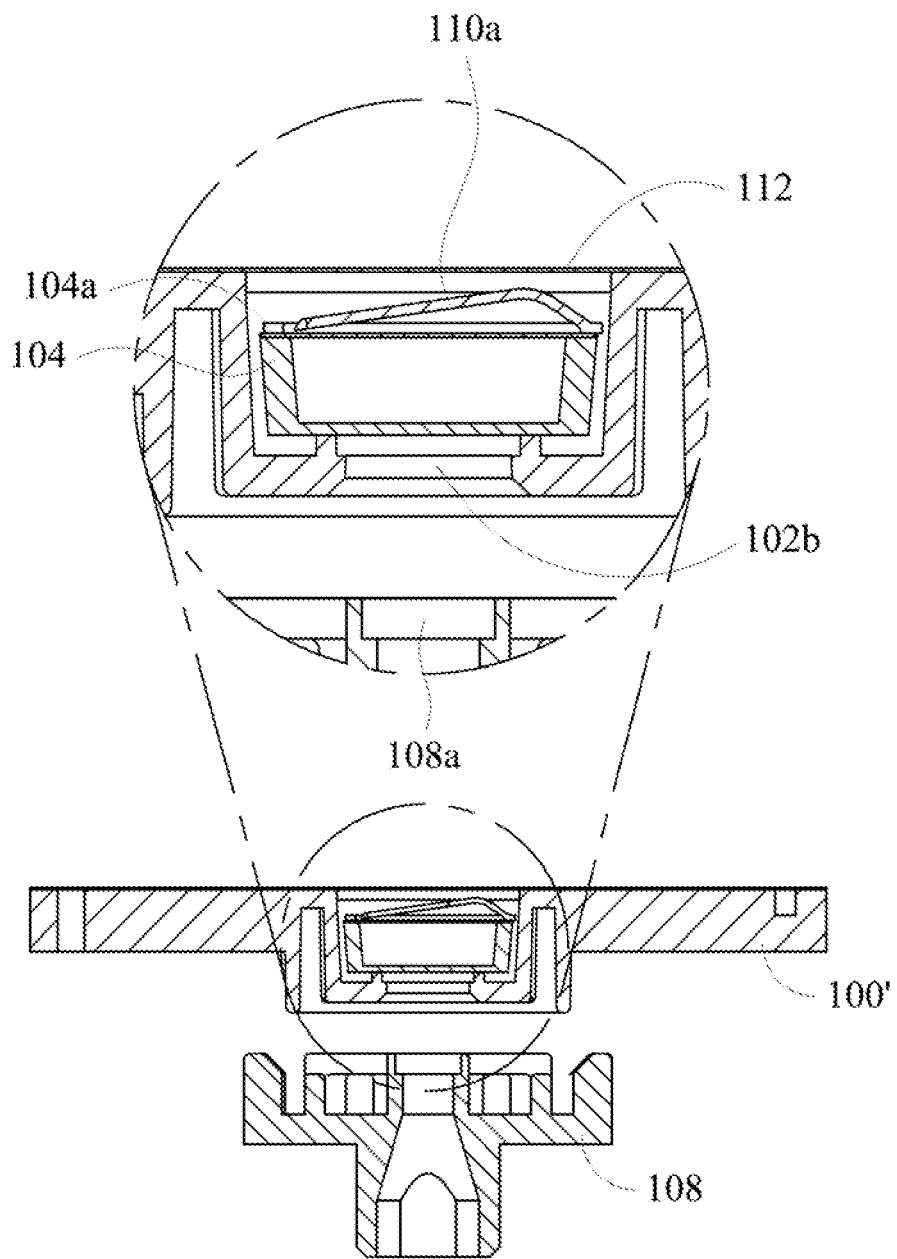
FIG. 5 illustrates a cross-sectional view of a centrifugal rotor and a driving rotor that are separated from each other according to another embodiment of this invention.
Figure 6:
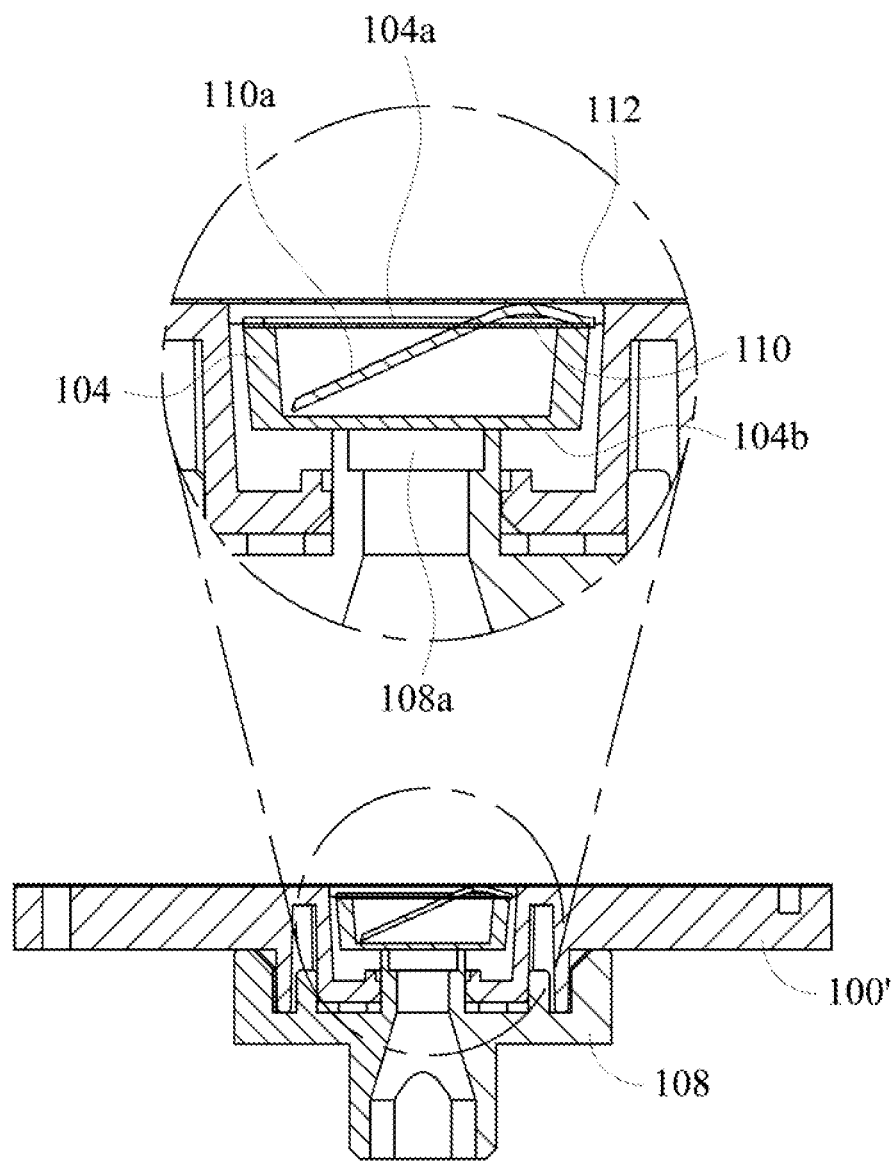
FIG. 6 illustrates a cross-sectional view of the centrifugal rotor and the driving rotor in FIG. 5 that are assembled.

Referring to both FIG. 5 and FIG. 6, FIG. 5 illustrates a cross-sectional view of a centrifugal rotor and a driving rotor that are separated from each other according to another embodiment of this invention, and FIG. 6 illustrates a cross-sectional view of the centrifugal rotor and the driving rotor in FIG. 5 that are assembled. The centrifugal rotor 100' as illustrated in FIG. 5 and FIG. 6 is different from the centrifugal rotor 100 in the piercing structure. When the centrifugal rotor 100' is not used to perform biochemical analysis, the centrifugal rotor 100' and the driving rotor 108 are separated, and a piercing member 110a of the piercing structure 110 cannot penetrate the seal film 104a of the diluent container 104 without an external push (referring to FIG. 5). When the centrifugal rotor 100' is used to perform biochemical analysis, the centrifugal rotor 100' and the driving rotor 108 are assembled. A central axis 108*a* of the driving rotor 108 is inserted through the bottom hole 102*b* of the centrifugal rotor 100' and coupled with a bottom part 104*b* of the diluent container 104 so as to lift the diluent container 104 to enable the piercing member 110*a* of the piercing structure 110 to cut the seal film 104*a* of the diluent container 104 to form a strip opening such that the diluents inside the container can be released (referring to FIG. 6).

Figure 7A:
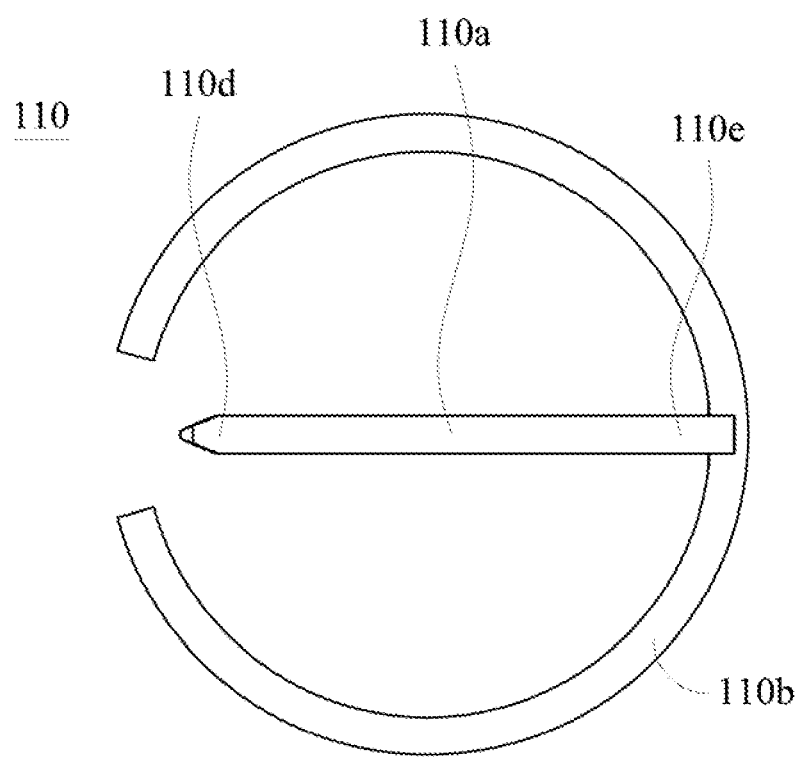
FIG. 7A illustrates a top view of a piercing structure according to another embodiment of this invention.
Figure 7B:
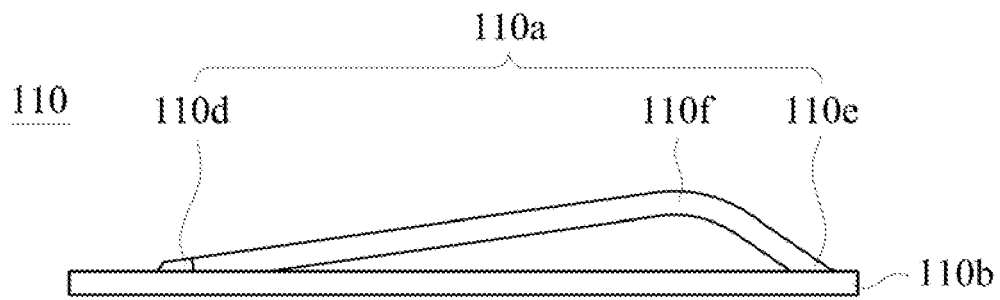
FIG. 7B illustrates a lateral view of the piercing structure in FIG. 7A.
Figure 7C:
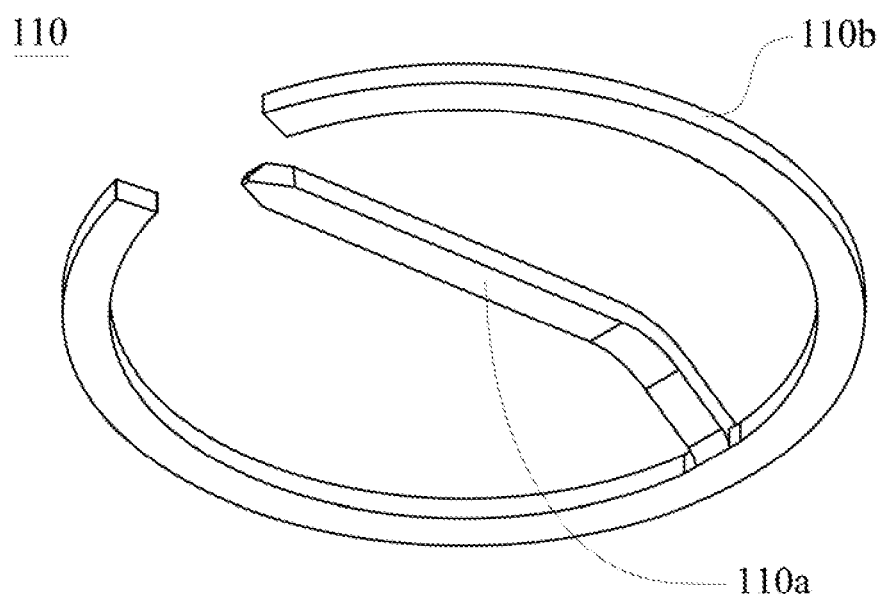
FIG. 7C illustrates a perspective view of the piercing structure in FIG. 7A.

Referring to FIG. 7A, FIG. 7B and FIG. 7C, FIG. 7A illustrates a top view of a piercing structure 110 according to another embodiment of this invention, FIG. 7B illustrates a lateral view of the piercing structure 110 in FIG. 7A, and FIG. 7C illustrates a perspective view of the piercing structure 110 in FIG. 7A. The piercing structure 110 is a piercing loop which comprises a C-shaped ring 110*b* and a piercing member 110*a*. The piercing member 110*a* has an end 110*e* coupled to the C-shaped ring 110*b* and another free end 110*d* which has a triangular tip (referring to FIG. 7A). Referring to FIG. 7B, the piercing member 110*a* protrudes out of a level within which the C-shaped ring 110*b* is located except two opposite ends of the piercing member 110*a*, and a bent part 110*f* is an upper point of the piercing member 110*a*. When the centrifugal rotor 100' and the driving rotor 108 are assembled, the bent part 110*f* of the piercing member 110*a* is in contact with the capping film 112 and the piercing member 110*a* is pressed to bend downwards so as to cut the seal film 104*a* of the diluent container 104 (referring to FIG. 6).

Figure 8A:
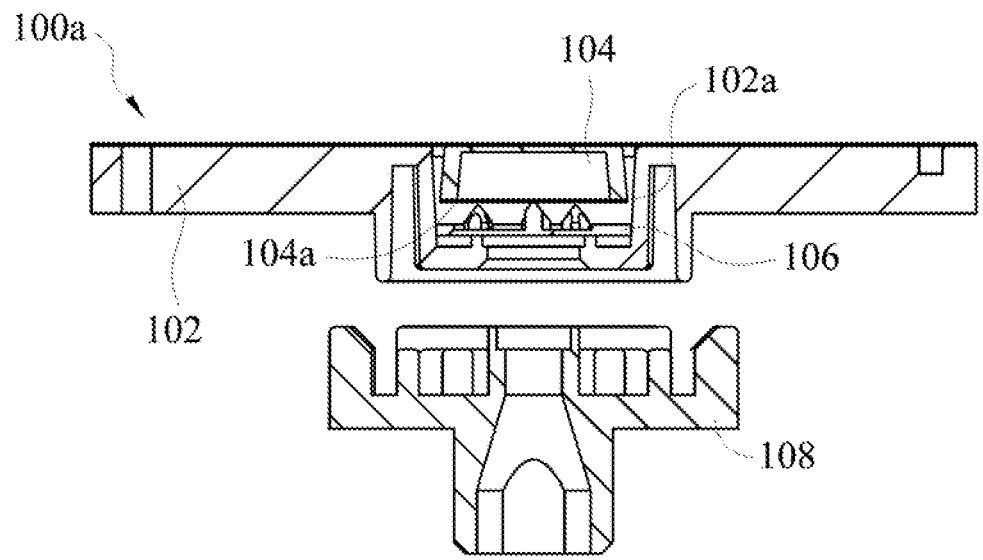
FIG. 8A illustrates a cross-sectional view of a centrifugal rotor and a driving rotor that are separated from each other according to still another embodiment of this invention.
Figure 8B:
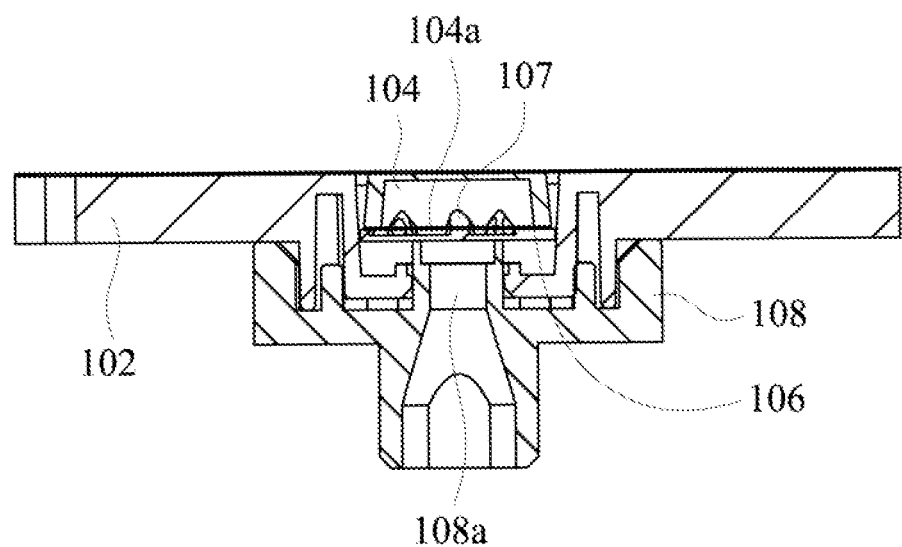
FIG. 8B illustrates a cross-sectional view of the centrifugal rotor and the driving rotor in FIG. 8A that are assembled.

Referring to both FIG. 8A. and FIG. 8B, FIG. 8A illustrates a cross-sectional view of a centrifugal rotor and a driving rotor that are separated from each other according to still another embodiment of this invention, and FIG. 8B illustrates a cross-sectional view of the centrifugal rotor and the driving rotor in FIG. 8A that are assembled. The centrifugal rotor 100*a* is different from the centrifugal rotor 100 in a position relationship between the diluent container 104 and the piercing structure 106. Within the centrifugal rotor 100*a*, the diluent container 104 is located above the piercing structure 106, and both the diluent container 104 and the piercing structure 106 are accommodated within the receiving cavity 102*a* of the rotor body 102. When the centrifugal rotor 100*a* is not used to perform biochemical analysis, the centrifugal rotor 100 and the driving rotor 108 are separated, and the piercing structure 106 cannot penetrate the seal film 104*a* of the diluent container 104 without an external push (referring to FIG. 8A). When the centrifugal rotor 100 is used to perform biochemical analysis, the centrifugal rotor 100 and the driving rotor 108 are assembled. The central axis 108*a* of the driving rotor 108 is inserted through the bottom hole 102*b* of the centrifugal rotor 100 and in contact with a bottom part of the piercing structure 106 so as to lift the cone 107 of the piercing structure 106 to penetrate the seal film 104*a* of the diluent container 104 (referring to FIG. 8B).

Figure 9A:
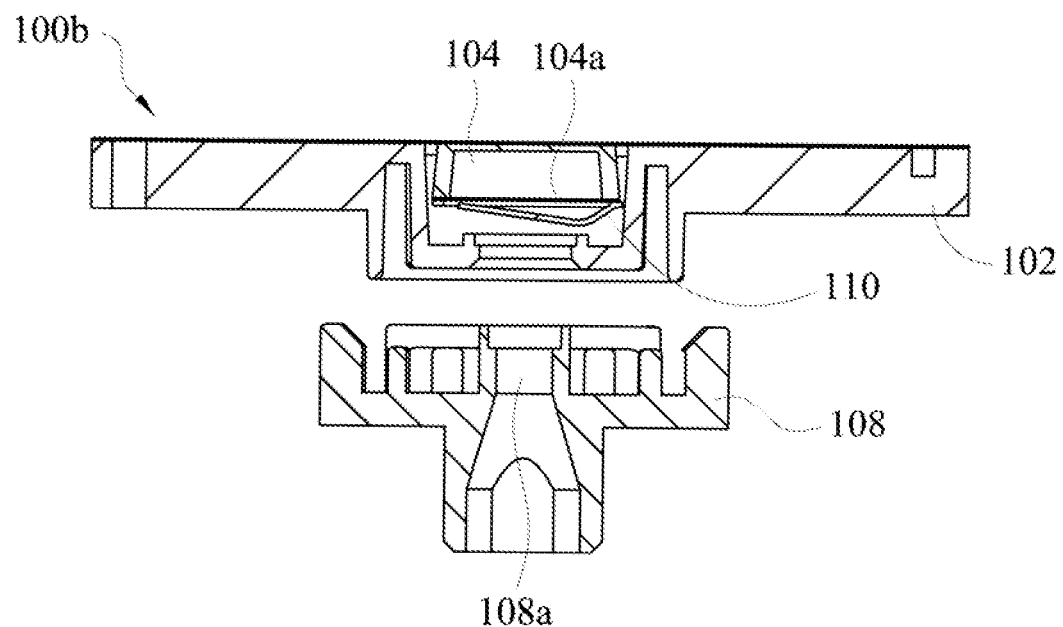
FIG. 9A illustrates a cross-sectional view of a centrifugal rotor and a driving rotor that are separated from each other according to yet another embodiment of this invention.
Figure 9B:
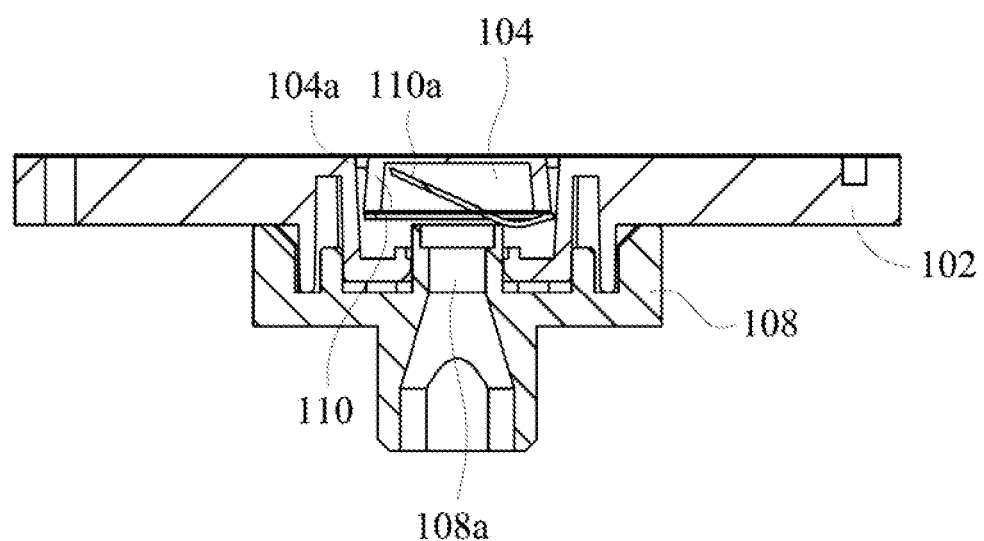
FIG. 9B illustrates a cross-sectional view of the centrifugal rotor and the driving rotor in FIG. 9A that are assembled.

Referring to FIG. 9A and FIG. 9B. FIG. 9A illustrates a cross-sectional view of a centrifugal rotor and a driving rotor that are separated from each other according to yet another embodiment of this invention, and FIG. 9B illustrates a cross-sectional view of the centrifugal rotor and the driving rotor in FIG. 9A that are assembled. The centrifugal rotor 100*b* is different from the centrifugal rotor 100' in a position relationship between the diluent container 104 and the piercing structure 110. Within the centrifugal rotor 100*b*, the diluent container 104 is located above the piercing structure 110, and both the diluent container 104 and the piercing structure 110 are accommodated within the receiving cavity 102*a* of the rotor body 102. When the centrifugal rotor 100*b* is not used to perform biochemical analysis, the centrifugal rotor 100*b* and the driving rotor 108 are separated, and the piercing structure 110 cannot penetrate the seal film 104*a* of the diluent container 104 without an external push (referring to FIG. 9A). When centrifugal rotor 100*b* is used to perform biochemical analysis, the centrifugal rotor 100*b* and the driving rotor 108 are assembled. A central axis 108*a* of the driving rotor 108 is inserted through a bottom hole of the centrifugal rotor 100*b* and coupled with a bottom part of the piercing structure 110 so as to lift and bend the piercing structure 110 to enable the piercing member 110*a* to cut the seal film 104*a* of the diluent container 104 to form a strip opening such that the diluents inside the container can be released (referring to FIG. 9B).

Figure 10A:
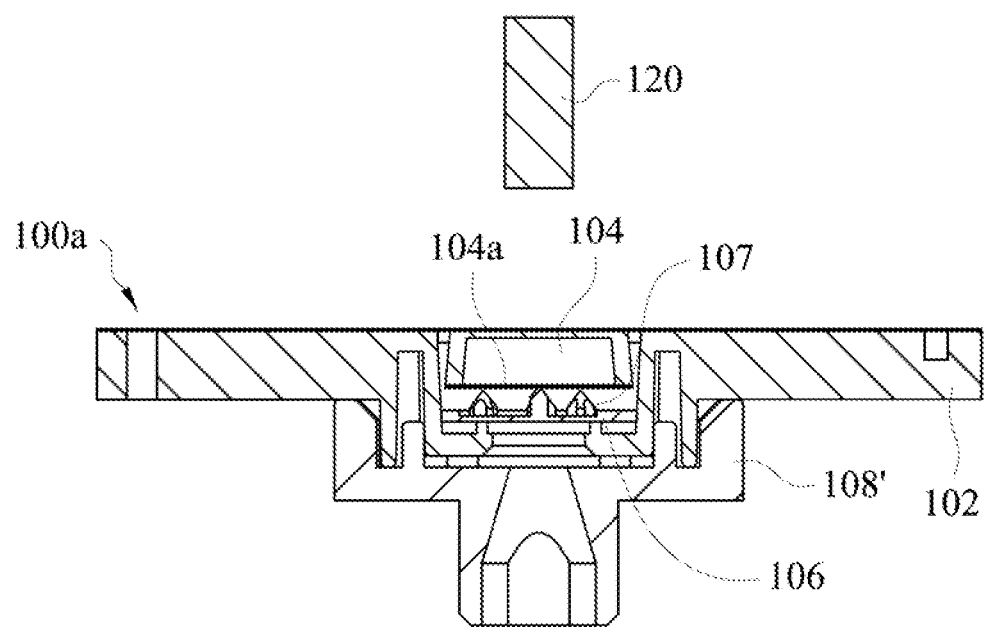
FIG. 10A illustrates a cross-sectional view of a centrifugal rotor and a driving rotor that are assembled but the actuator is not pressed according to still another embodiment of this invention.
Figure 10B:
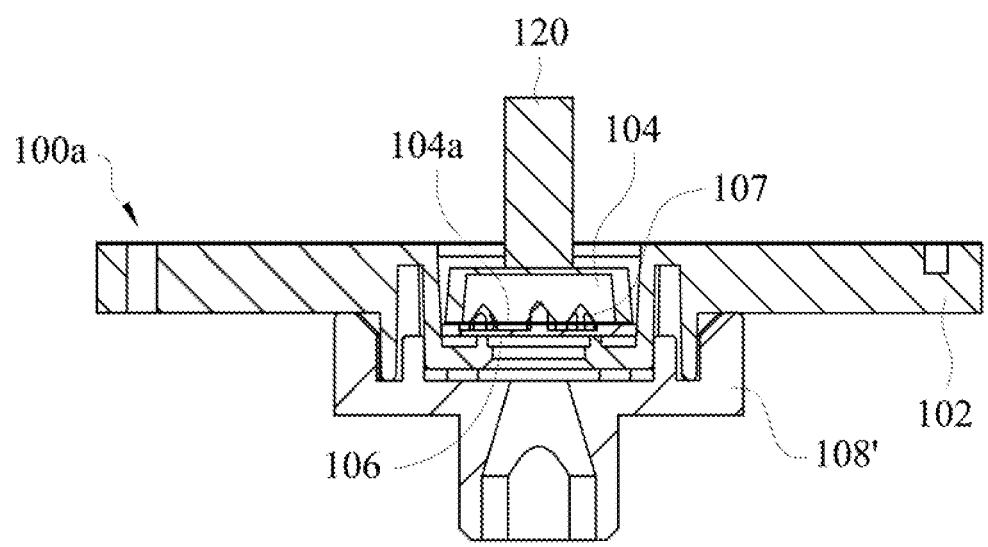
FIG. 10B illustrates a cross-sectional view of a centrifugal rotor and a driving rotor that are assembled but the actuator is pressed according to still another embodiment of this invention.

Referring to FIG. 10A and FIG. 10B, FIG. 10A illustrates a cross-sectional view of a centrifugal rotor and a driving rotor that are assembled but the actuator is not pressed according to still another embodiment of this invention, and FIG. 10B illustrates a cross-sectional view of a centrifugal rotor and a driving rotor that are assembled but the actuator is pressed according to still another embodiment of this invention. This embodiment is different from the embodiment as illustrated in FIG. 8A and FIG. 8B in that the piercing structure 106 is not enabled to penetrate the seal film 104*a* of the diluent container 104 when the centrifugal rotor 100*a* and the driving rotor 108' are assembled. Therefore, an actuator 120 is used as an external push to press a top portion of the diluent container 104 and force the cone 107 of the piercing structure 106 to penetrate the seal film 104*a* of the diluent container 104 (referring to FIG. 10B).

Figure 11A:
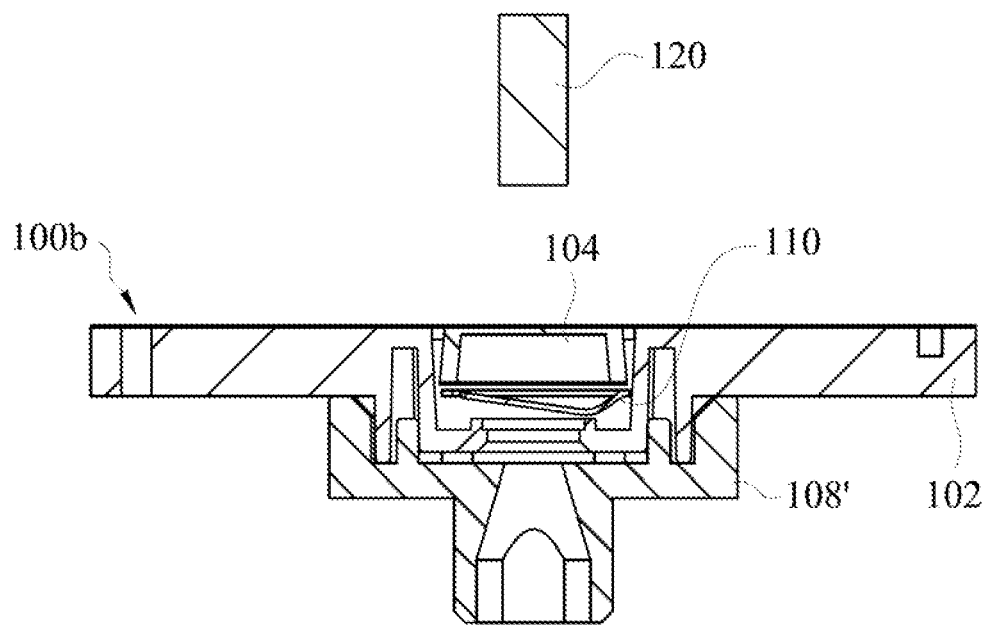
FIG. 11A illustrates a cross-sectional view of a centrifugal rotor and a driving rotor that are assembled but the actuator is not pressed according to yet another embodiment of this invention.
Figure 11B:
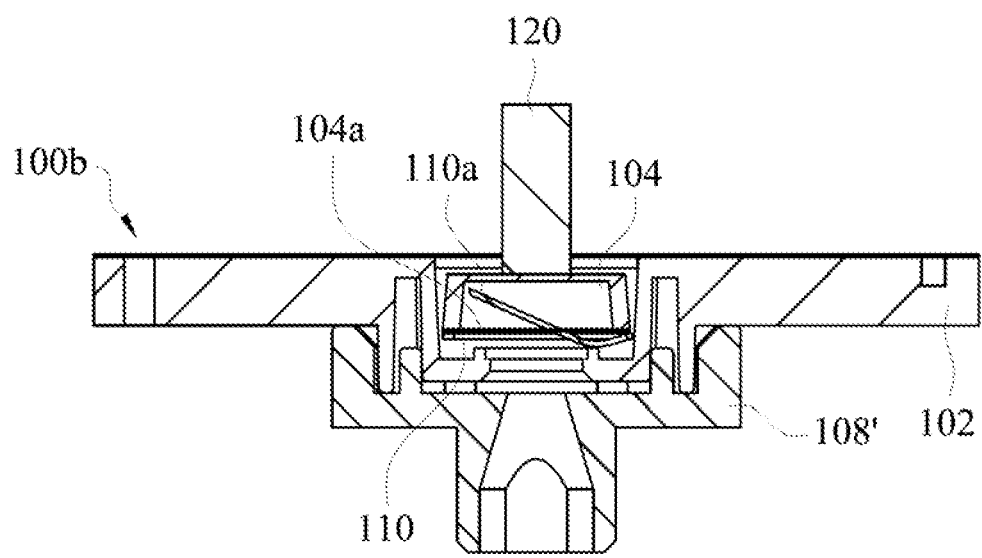
FIG. 11B illustrates a cross-sectional view of a centrifugal rotor and a driving rotor that are assembled but the actuator is pressed according to yet another embodiment of this invention.

Referring to FIG. 11A and FIG. 11B, FIG. 11A illustrates a cross-sectional view of a centrifugal rotor and a driving rotor that are assembled but the actuator is not pressed according, to yet another embodiment of this invention, and FIG. 11B illustrates a cross-sectional view of a centrifugal rotor and a driving rotor that are assembled but the actuator is pressed according to yet another embodiment of this invention. This embodiment is different from the embodiment as illustrated in FIG. 9A and FIG. 9B in that the piercing structure 110 is not enabled to penetrate the seal film 104*a* of the diluent container 104 when the centrifugal rotor 100*b* and the driving rotor 108' are assembled. Therefore, an actuator 120 is used as an external push to press as top portion of the diluent container 104 and force the piercing member 110*a* of the piercing structure 110 to cut the seal film 104*a* of the diluent container 104 (referring to FIG. 11B).

According to the above-discussed embodiments, the centrifugal rotor disclosed herein is equipped with a piercing structure to penetrate a seal film of the diluent container, rather than removing the seal film of the diluent container manually. Therefore, the piercing structure design makes it easier to perform biochemical analysis, and the diluted solution can be released when needed and prevented from being volatile or contaminated.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the follow claims.

What is claimed is:

1. A centrifugal rotor comprising:
   a rotor body having a receiving cavity;
   a diluent container disposed within the receiving cavity and having a seal film;
   a piercing structure disposed within the receiving cavity and in contact with the seal film; and
   a capping film disposed over the diluent container and the piercing structure for securing the diluent container and the piercing structure within the receiving cavity.

2. The centrifugal rotor of claim 1, wherein the piercing structure is a cover which comprises a plurality of cones facing the seal film.

3. The centrifugal rotor of claim 2, wherein one of the cones is disposed at a center of the cover.

4. The centrifugal rotor of claim 3, wherein the cone at the center of the cover is higher than the remaining cones of the cover.

5. The centrifugal rotor of claim 2, wherein each cone comprises at least one concave groove.

6. The centrifugal rotor of claim 2, wherein the cover has a concave liquid guiding area within which the cones are located.

7. The centrifugal rotor of claim 1, wherein the piercing structure is a piercing loop which comprises a C-shaped ring and a piercing member, having an end coupled to the C-shaped ring.

8. The centrifugal rotor of claim 7, wherein a free end of the piercing member comprises a triangular tip.

9. The centrifugal rotor of claim 7, wherein the piercing member protrudes out of a level within which the C-shaped ring is disposed except two opposite ends of the piercing member.

10. The centrifugal rotor of claim 1, wherein the seal film is a plastic film or a metallic film.

11. The centrifugal rotor of claim 1, wherein the piercing structure is disposed above the diluent container.

12. The centrifugal rotor of claim 11, wherein the receiving cavity has a bottom bole that is aligned with the diluent container.

13. The centrifugal rotor of claim 1, wherein the diluent container is disposed above piercing structure.

14. The centrifugal rotor of claim 13, wherein the receiving cavity has a bottom hole that is aligned with the diluent container.

* * * * *